United States Patent
Heinzel

Patent Number: 5,906,945
Date of Patent: May 25, 1999

[54] METHOD FOR TESTING AND DETERMINING THE ALLOY CLASS OF AN ALUMINUM ALLOY

[75] Inventor: Ulrich Heinzel, Bremen, Germany

[73] Assignee: Daimler-Benz Aerospace Airbus GmbH, Hamburg, Germany

[21] Appl. No.: 08/940,633

[22] Filed: Sep. 30, 1997

[30] Foreign Application Priority Data

Oct. 1, 1996 [DE] Germany .......................... 196 40 500

[51] Int. Cl.$^6$ .................................................. G01N 33/20
[52] U.S. Cl. ............................ 436/73; 436/166; 436/182
[58] Field of Search ............................. 436/73, 164, 166, 436/179, 182

[56] References Cited

U.S. PATENT DOCUMENTS

| | | | |
|---|---|---|---|
| 3,652,225 | 3/1972 | Coffin, Jr. et al. .......................... | 436/5 |
| 3,701,631 | 10/1972 | Wilson ................................. | 436/73 X |
| 4,783,417 | 11/1988 | Genna ...................................... | 436/73 |

FOREIGN PATENT DOCUMENTS 2730813  2/1978  Germany .
3636820  5/1988  Germany .

OTHER PUBLICATIONS

F.J. Bowen *Steel*, 1952, pp. 67&74.
W.P. Iverson *Nature* 1967, 213, 486–487

*Primary Examiner*—Arlen Soderquist
*Attorney, Agent, or Firm*—W. F. Fasse; W. G. Fasse

[57] ABSTRACT

A method for testing and determining the alloy class of an aluminum alloy may be simply and easily carried out, for unequivocally determining the correct alloy class among the aluminum alloy classes 2XXX, 5XXX or 6XXX, and 7XXX, of the test sample. According to the method, the material sample is dissolved in hydrochloric acid (HCL) to prepare a first solution, then nitric acid ($HNO_3$) is added drop-wise to the first solution in order to cause oxidation of any insoluble copper (Cu) therein and form a second solution, then a potassiumhexacyanoferrate (II) solution ($K_4[Fe(CN)_6]$) is added to the second solution to bring about a discoloration and precipitation reaction and form a final resulting solution. Finally, the applicable alloy class of the tested material sample is determined by visually categorizing the color and precipitation state of the resulting solution. A brown cloudy solution indicates a 2XXX alloy, a gray-green cloudy solution indicates a 7XXX alloy, and a blue or green transparent solution indicates a 5XXX or 6XXX alloy.

24 Claims, 3 Drawing Sheets

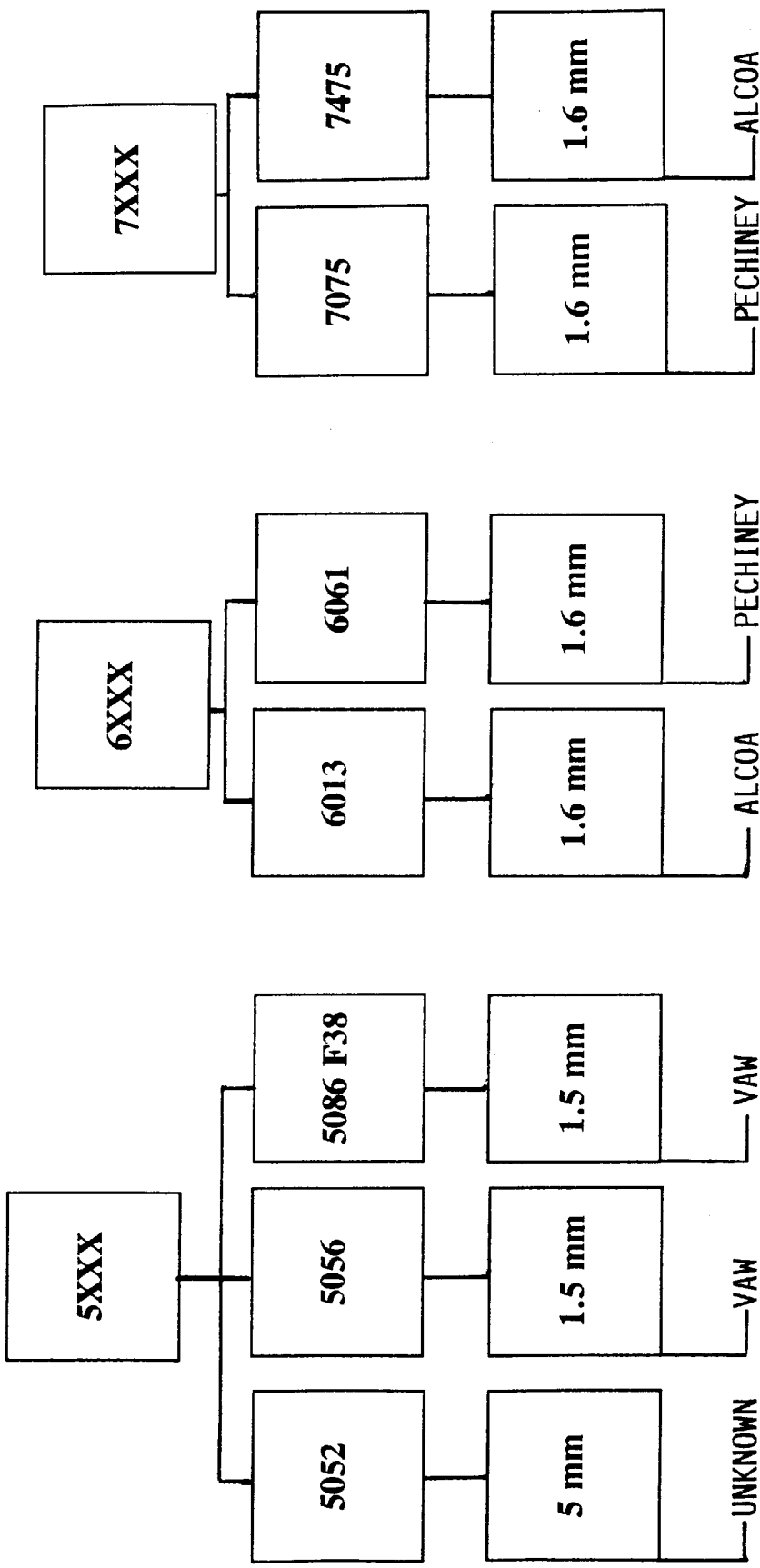

METHOD FOR TESTING AND DETERMINING THE ALLOY CLASS OF AN ALUMINUM ALLOY

FIELD OF THE INVENTION

The invention relates to a method for testing and determining the alloy class of an aluminum alloy, and especially aluminum alloy sheet materials used in aircraft construction.

BACKGROUND INFORMATION

In servicing, repairing, or carrying out maintenance on aircraft, it is often necessary to determine the type or class of aluminum alloy of an aircraft component, among a plurality of possible different typical aluminum alloys that are used in the structure of an aircraft. This is especially true if documentation regarding repair materials that are to be used does not exist or is not available. In this situation, a complete chemical analysis of the aluminum alloy material would give a clear and precise answer regarding the alloy composition, but such a complete chemical analysis is expensive, complicated, and time consuming and thus not suitable to be used each time the alloy type or class must be determined. Moreover, it is generally sufficient to determine only the general alloy type or class of the material, and it is not necessary to determine the precise alloy composition in most cases.

For this purpose, it has become generally known in the art to use a so-called spot method test, but in actual practice such a spot method test has been found to be unsuitable for the following reasons. In order to carry out the spot method test to identify various aluminum material groups, different test solutions are applied onto the metal surface that is to be tested, in a sequence of individual steps. After each step, the person carrying out the test must reach an opinion as to the type of reaction that occurred due to the interaction of the respective test solution and the aluminum material, based on observed color changes and the like, and in response thereto the person must then decide which test solution is to be used in the next step of the test sequence.

The above described spot test method is relatively time consuming and also complicated and cumbersome due to the sequence of steps that must be carried out using three different test solutions. It is a further disadvantage in the known method, that after each step, the person carrying out the test must once again correctly determine and decide which step using which solution should be carried out next. In this context, any incorrect interpretation of the results in any one of the steps will lead to an incorrect test sequence path that will necessarily cause an erroneous overall result of the test. A further disadvantage is that the color changes resulting from each test step are rather difficult to detect and to distinguish or categorize. For example, color designations such as "gray" or "no discoloration" are freely open to a wide degree of personal subjective interpretation when observed on the metal surface. Moreover, the color change or discoloration resulting after some steps is best recognizable if the testing solution is carefully dabbed off using a cloth without disturbing the material surface, while in other cases the drop of testing solution should be allowed to remain on the metal surface while observing the discoloration.

A further substantial disadvantage or defect in the known method is that one of the described branches of the testing sequence or testing program gives provably false results. Namely, it has been determined that plated and unplated sheet alloy materials of the type or class 7XXX do not react the same way when tested using a hydrochloric acid cadmium sulfate solution. Thus, at least for materials of the alloy class 7XXX, the known drop or spot method test is not functional when carried out in the above described manner.

SUMMARY OF THE INVENTION

In view of the above, it is an object of the invention to provide a simple and rapid method for testing an aluminum alloy, and unambiguously and reliably classifying the tested aluminum alloy into a proper alloy class. Further objects of the invention are to avoid or overcome the disadvantages of the prior art, and to achieve additional advantages, as evident from the present description.

The above objects have been achieved in a method for testing and determining the alloy class of an aluminum alloy according to the invention, including the following steps. In a first step, a material sample is removed or extracted from the aluminum alloy material, and particularly an aluminum alloy sheet metal that is to be tested or identified. Next, the material sample is dissolved in hydrochloric acid (HCl). Then, nitric acid ($HNO_3$) is added in a drop-wise manner to the solution of the material sample dissolved in the hydrochloric acid, in order to cause oxidation of any unsoluble copper (Cu) in the solution. Next, a potassium-hexacyanoferrate (II) solution ($K_4[Fe(CN)_6]$) is added to the solution of the material sample, the hydrochloric acid, and the nitric acid, to bring about a discoloration and precipitation reaction as applicable. Finally, the respective alloy class, namely a first class 2XXX, a second class 5XXX or 6XXX, or a third class 7XXX, of the aluminum alloy material being tested is determined based on and responsive to the discoloration and precipitation reaction that occurs.

Advantageously, the sequence or program of steps to be carried out according to the method of the invention is linear and fixed. This sequence essentially comprises three successive steps, which always remain the same in the same sequence under all test conditions, whereby no decisions or interim determinations need be made during the course of carrying out the test. Thus, the inventive test method completely excludes the possibility of progressing along an inappropriate and thus misleading and error-causing test sequence path. A further advantage of the method according to the invention is seen in that the colors and precipitation conditions resulting at the end of the test are clearly, distinctly, and unambiguously distinguishable from one another, so that the correct alloy class may be accurately and reliably recognized. Another advantage is seen in that at least two of the three test solutions used in the test method according to the invention are readily available in ordinary trade, and may be obtained or prepared in the necessary concentrations simply by diluting with distilled water as necessary. Thus, the complexity, effort, and cost of carrying out the method is relatively low compared to any prior art testing methods.

According to a detailed feature of the invention, the intermediate solution of the material sample, the hydrochloric acid, and the nitric acid can be diluted using distilled water for improving the effectiveness of the test reactions and the ease of interpreting the resulting color and precipitation conditions.

Details of a particular embodiment of the method according to the invention are as follows. In the first step, a material sample of from 20 mg to 50 mg material mass is dissolved in 2 ml of hydrochloric acid (HCl). After the evolution of gases has ended in the solution of the material sample in hydrochloric acid, five drops of nitric acid ($HNO_3$) are added immediately thereto. Then, distilled water is added to dilute the solution, and 1.5 ml of a potassium-hexacyanoferrate (II) solution ($K_2[Fe(CN)_6]$) is added to the diluted solution of the material sample, hydrochloric acid and nitric acid.

Further according to the invention, the material sample may be removed from the aluminum alloy material, and particularly an aluminum alloy sheet material that is to be classified, using a hollow boring bit, and particularly a hollow boring bit having a diameter of 3 mm, for example. The hollow-bored core then forms the material sample. Alternatively, boring or drilling chips, shavings or dust particles can be used as the material sample. If the above mentioned particular hollow boring bit having a 3 mm diameter is used to provide a hollow-bored sample <2.6 mm thick, then the resulting solution of the material sample, hydrochloric acid and nitric acid is diluted using 6 ml of distilled water, while if a hollow-bored sample a $\geq 2.6$ mm in thickness is used, then the solution is diluted using 10 ml of distilled water.

A half-concentration 16% hydrochloric acid solution usable in the method according to the invention may easily be prepared, for example by diluting 50 ml of a standard stock 32% concentrated hydrochloric acid available in the trade with 50 ml of distilled water. A particular 65% concentrated nitric acid solution usable in the method according to the invention is directly available as a stock item in the trade. The particular 2% concentration potassiumhexacyanoferrate (II) solution ($K_4[Fe(CN)_6]$) used according to the invention can easily be produced by dissolving 2 g of potassium hexacyanoferrate in 100 ml of distilled water. The necessary equipment for preparing these solutions and carrying out the test is quite simple, and may consist of standard reagent vessels having dimensions 16×160 mm, a 3 ml plastic pipette, a weighing scale with an accuracy and precision of 10 mg, and a measuring cylinder e.g. of 100 ml volume.

BRIEF DESCRIPTION OF THE DRAWINGS

In order that the invention may be clearly understood, it will now be described in connection with an example embodiment of the invention with reference to the drawings, wherein:

FIG. 3 is a block diagram schematically representing the particular material characteristics of test samples within the alloy class 5XXX that were tested according to the invention;

FIG. 4 is a block diagram schematically representing the particular material characteristics of test samples within the alloy class 6XXX that were tested according to the invention; and FIG. 5 is a block diagram schematically representing the particular material characteristics of test samples within the alloy class 7XXX that were tested according to the invention.

DETAILED DESCRIPTION OF PREFERRED EXAMPLE EMBODIMENTS AND OF THE BEST MODE OF THE INVENTION

Figure 1:
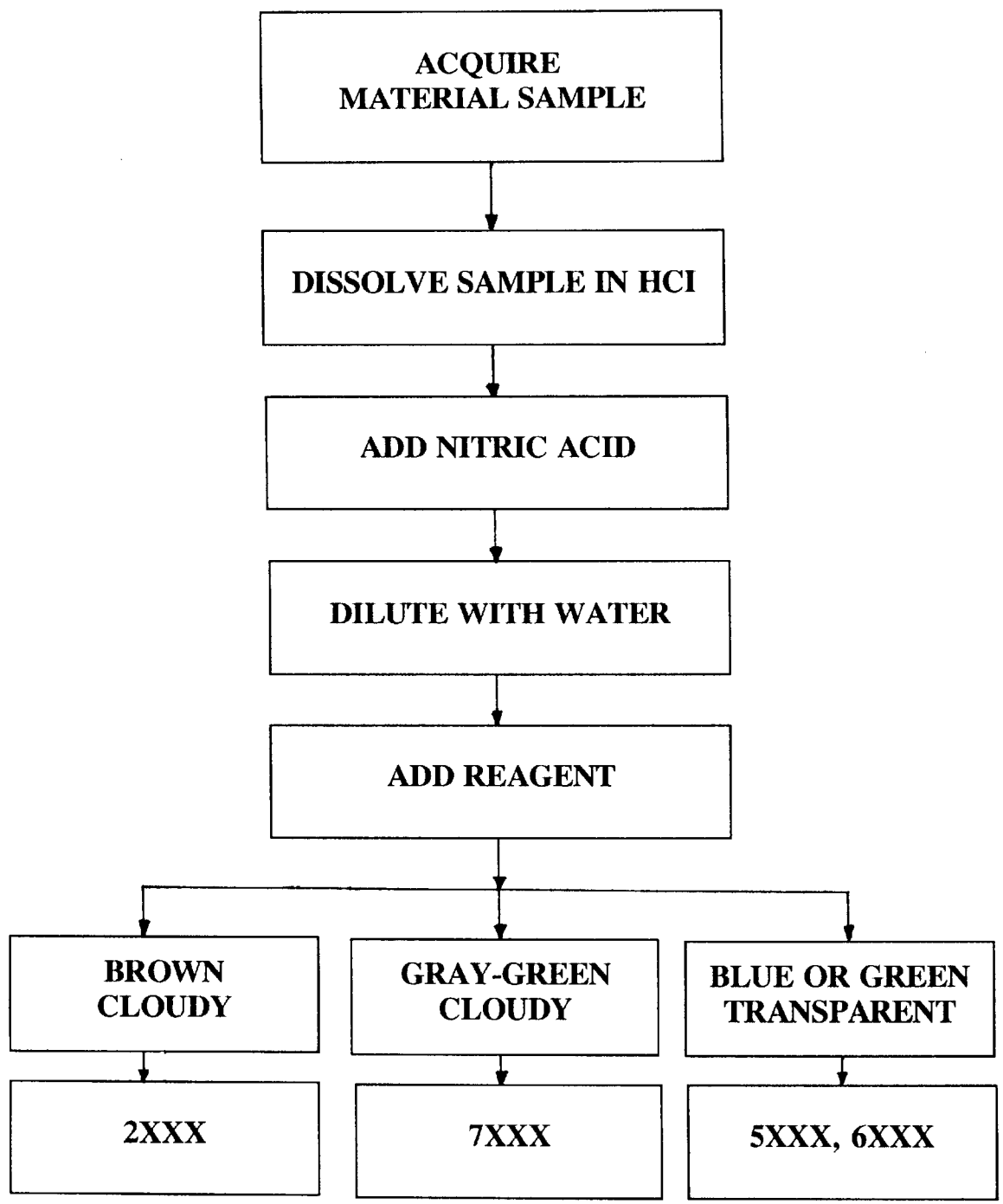
FIG. 1 is a block flow diagram showing the steps of a testing method according to the invention.

FIG. 1 shows blocks schematically representing the sequence of steps carried out in an example of the present inventive method. In a first step, a material sample is acquired. In a second step, the material sample is dissolved in hydrochloric acid. In a third step, nitric acid is added to the previous solution. In a fourth step, the resulting solution is diluted with distilled water. In a fifth step, a potassium-hexacyanoferrate (II) solution ($K_4[Fe(CN)_6]$) as a reagent is added to the diluted solution.

Following the fifth step, the test result is determined visually in a sixth step, represented by three possible test results. Namely, if the final resulting solution is brown and cloudy, then it has been determined that the material sample is of the aluminum alloy class 2XXX; if the final resulting solution is gray-green and cloudy, then it has been determined that the material sample is of the aluminum alloy class 7XXX; and if the final resulting solution is blue or green and transparent, then it has been determined that the material sample is of the aluminum alloy class 5XXX or 6XXX.

In order to verify the accuracy and general applicability of the inventive testing method for testing and determining the alloy class of aluminum alloy materials, a great number of sample materials of known alloy classes or types 2XXX, 5XXX, 6XXX, and 7XXX were tested according to the method. Among the samples, the material thickness, the specific chemical composition or alloy designation, as well as the respective manufacturer of the sheet metal sample materials varied as represented in an overview manner in FIGS. 2 to 5.

Figure 2:
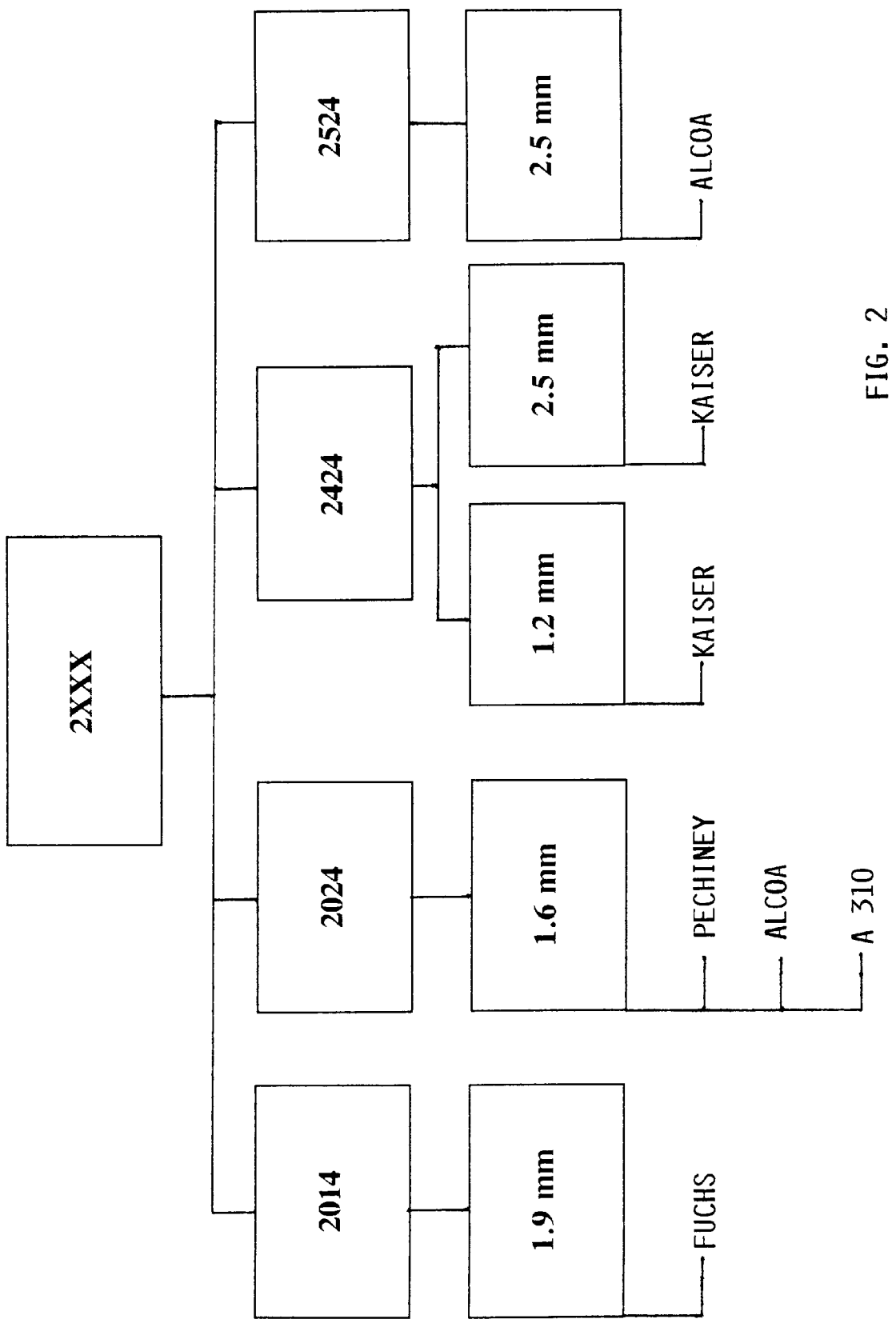
FIG. 2 is a block diagram schematically representing the particular material characteristics of test samples within the alloy class 2XXX that were tested according to the invention.

In each of FIGS. 2 to 5, the top plane or row designates the general aluminum alloy class of the respective samples, the second plane or row represents the specific alloy designation (e.g. 2014, 2024, 2424, etc.) of the respective samples based on the known chemical composition thereof, the third plane or row represents the sample thickness of the respective samples, and the fourth plane represents the particular manufacturer of the respective test samples. For example, as shown in FIG. 2, three samples having a 1.6 mm thickness of a 2024 aluminum alloy respectively manufactured by Pechiney, Alcoa, and from an Airbus A310 aircraft were tested. Also, two samples respectively having a thickness of 1.2 mm and 2.5 mm of 2424 aluminum alloy manufactured by Kaiser were tested, for example. The remaining samples are similarly described or categorized in the FIGS. 2 to 5.

All of the samples were tested under the test conditions described above herein. The test results were visually determined by observing the final resulting solutions contained in reagent vessels placed in front of a white background. For all of the tested samples, the results all consistently and accurately confirmed the actual known alloy composition classes of the test samples. Namely, for all of the test samples, a brown and cloudy final solution indicated an alloy of the class 2XXX, a gray-green and cloudy final solution indicated an alloy of the class 7XXX, and a blue or green and completely transparent solution indicated an alloy of the class 5XXX or 6XXX.

It was further determined that the test method is preferably applicable to test samples having from 20 to 50 mg of metal per test. To reach this conclusion, 50 hollow-bored test samples having a 3 mm diameter and a thickness in the range from 1.2 to 2.6 mm were weighed, i.e. their mass was determined, and then these test samples were subjected to the present testing method to confirm its applicability.

The present method according to the invention is not limited to testing aluminum alloys used for sheet metal structures in aircraft construction. Rather, the present method is applicable in the same manner to all aluminum alloys, for example aluminum alloy materials used in the fields of light metal construction, automobile construction, or the like.

Although the invention has been described with reference to specific example embodiments, it will be appreciated that it is intended to cover all modifications and equivalents within the scope of the appended claims. It should also be understood that the present disclosure includes all possible combinations of any individual features recited in any of the appended claims.

What is claimed is:

1. A method of determining the alloy class of an aluminum alloy material, comprising the following steps:
   a) dissolving an aluminum alloy material sample in hydrochloric acid to prepare a first solution;
   b) adding nitric acid to said first solution to prepare a second solution;
   c) adding a potassiumhexacyanoferrate (II) solution to said second solution to prepare a third solution having a color; and
   d) determining an alloy class of said aluminum alloy sample material responsive to and associated with said color of said third solution.

2. The method according to claim 1, wherein said color is brown and said alloy class determined in said step d) is 2XXX.

3. The method according to claim 1, wherein said color is gray-green and said alloy class determined in said step d) is 7XXX.

4. The method according to claim 1, wherein said color is blue or green and said alloy class determined in said step d) is 5XXX or 6XXX.

5. The method according to claim 1, wherein said third solution further has an observable precipitation state of either clear or cloudy, and wherein said determining of said alloy class is carried out further responsive to and associated with said precipitation state of said third solution.

6. The method according to claim 5, wherein said color and said precipitation state are selected from the group consisting of brown and cloudy, gray-green and cloudy, blue and transparent, and green and transparent.

7. The method according to claim 6, wherein said color is brown and said precipitation state is cloudy, and said alloy class determined in said step d) is 2XXX.

8. The method according to claim 6, wherein said color is gray-green and said precipitation state is cloudy, and said alloy class determined in said step d) is 7XXX.

9. The method according to claim 6, wherein said color is blue or green and said precipitation state is transparent, and said alloy class determined in said step d) is 5XXX or 6XXX.

10. The method according to claim 5, further comprising an additional step of diluting said second solution by adding distilled water thereto, before said step c).

11. The method according to claim 10, wherein:
    said step a) comprises dissolving 20 mg to 50 mg of said aluminum alloy material sample in 2 ml of said hydrochloric acid to prepare said first solution, which evolves gas,
    said step b) is only carried out after cessation of said evolving of gas, and comprises the immediate addition of five drops of nitric acid to said first solution to prepare said second solution, and
    said step c) comprises adding 1.5 ml of said potassium-hexacyanoferrate (II) solution to said second solution after said additional step of diluting said second solution.

12. The method according to claim 5, further comprising a preliminary step of acquiring said sample from an aluminum alloy material that is to be tested.

13. The method according to claim 12, wherein said preliminary step of acquiring said sample comprises boring said sample from said aluminum alloy material using a hollow core boring tool to provide a hollow-bored core sample as said sample.

14. The method according to claim 13, wherein said hollow-bored core sample has a thickness less than 2.6 mm, and further comprising an additional step of diluting said second solution by adding 6 ml of distilled water thereto.

15. The method according to claim 13, wherein said hollow-bored core sample has a thickness of at least 2.6 mm, and further comprising an additional step of diluting said second solution by adding 10 ml of distilled water thereto.

16. The method according to claim 5, wherein said hydrochloric acid is a 16% concentrated solution of HCl.

17. The method according to claim 5, wherein said nitric acid is a 65% concentrated solution of $HNO_3$.

18. The method according to claim 5, wherein said potassiumhexacyanoferrate (II) solution is a 2% concentrated solution of ($K_4[Fe(CN)_6]$).

19. The method according to claim 5, wherein said aluminum alloy material sample contains at least aluminum and copper, wherein at least some of said copper does not dissolve in said hydrochloric acid in said step a), and wherein said step b) comprises adding said nitric acid drop-by-drop to said first solution in an amount just sufficient and so as to oxidize said non-dissolved copper.

20. The method according to claim 5, consisting essentially of said steps a), b), c) and d) and an additional step of diluting said second solution with distilled water between said steps b) and c).

21. The method according to claim 1, wherein said steps a), b), c) and d) are carried out in a container.

22. The method according to claim 1, wherein said step d) is carried out by visually observing said color of said third solution with said third solution placed in front of a white background.

23. The method according to claim 1, wherein:
    said step a) comprises dissolving 20 mg to 50 mg of said aluminum alloy material sample in 2 ml of said hydrochloric acid to prepare said first solution, which evolves gas,
    said step b) is only carried out after cessation of said evolving of gas and comprises the immediate addition of five drops of said nitric acid to said first solution to prepare said second solution, and
    said step c) comprises adding 1.5 ml of said potassium-hexacyanoferrate (II) solution to said second solution.

24. The method according to claim 1, wherein said alloy class is any one of a first alloy class 2XXX, a second alloy class 5XXX or 6XXX, and a third alloy class 7XXX.

* * * * *